United States Patent
Yada et al.

(10) Patent No.: US 7,094,921 B2
(45) Date of Patent: Aug. 22, 2006

(54) METHOD FOR STORING (METH)ACRYLIC ACID OR (METH)ACRYLIC ESTERS

(75) Inventors: Shuhei Yada, Yokkaichi (JP); Kenji Takasaki, Yokkaichi (JP); Yoshiro Suzuki, Yokkaichi (JP); Yasushi Ogawa, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 11/006,803

(22) Filed: Dec. 8, 2004

(65) Prior Publication Data

US 2005/0192463 A1  Sep. 1, 2005

Related U.S. Application Data

(63) Continuation of application No. PCT/JP04/15479, filed on Oct. 20, 2004.

(30) Foreign Application Priority Data

Feb. 27, 2004 (JP) .............................. 2004-053313

(51) Int. Cl.
    *C07C 67/48* (2006.01)
    *C07C 69/52* (2006.01)
    *C07C 57/02* (2006.01)
    *C07C 51/42* (2006.01)

(52) U.S. Cl. ...................... 560/205; 560/218; 562/598; 562/600

(58) Field of Classification Search ..................... None
    See application file for complete search history.

(56) References Cited

U.S. PATENT DOCUMENTS

2003/0205451 A1 * 11/2003 Briegel et al. .................. 203/1

FOREIGN PATENT DOCUMENTS

JP   2003-231661   8/2003

\* cited by examiner

*Primary Examiner*—Paul A. Zucker
(74) *Attorney, Agent, or Firm*—Nixon & Vanderhye P.C.

(57) ABSTRACT

There is provided a method for storing (meth)acrylic acid or (meth)acrylic esters in a storage tank for receiving or discharging the (meth)acrylic acid or (meth)acrylic esters, which is capable of storing the (meth)acrylic acid or (meth) acrylic esters for a long period of time. According to the method of the present invention, upon storing the (meth) acrylic acid or (meth)acrylic esters in the storage tank for receiving or discharging the (meth)acrylic acid or (meth) acrylic esters, a concentration of suspended particulate matters contained in a gas phase portion of the storage tank is controlled to not more than 0.01 mg/m$^3$.

3 Claims, No Drawings

METHOD FOR STORING (METH)ACRYLIC ACID OR (METH)ACRYLIC ESTERS

This application is a continuation of the US national phase of international application PCT/JP04/15479 filed 20 Oct. 2004. The entire content of this application is incorporated herein by reference.

TECHNICAL FIELD

The present invention relates to a method for storing (meth)acrylic acid or (meth)acrylic esters. Meanwhile, in the present specification, the "(meth)acrylic acid" generally includes acrylic acid and methacrylic acid, and the "(meth)acrylic esters" generally include acrylic esters and methacrylic esters.

BACKGROUND ARTS

The (meth)acrylic acid and (meth)acrylic esters are easily-polymerizable compounds. When the (meth)acrylic acid or (meth)acrylic esters are stored in a storage tank for receiving or discharging the (meth)acrylic acid and (meth)acrylic esters for a long period of time, undesirable polymerization thereof tends to be frequently caused in the storage tank, resulting in problems such as production of insoluble polymers.

For the purpose of preventing production of the insoluble polymers in the storage tank, a polymerization inhibitor is added to the (meth)acrylic acid or (meth)acrylic esters stored therein. However, the polymerization inhibitor added is present only in a liquid phase in the storage tank, but is absent in a gas phase therein. In order to prevent production of polymers in such a gas phase, there are conventionally known the methods of blowing or sucking, as a polymerization-inhibiting gas, an oxygen-containing gas, for example, a mixed gas of an inert gas such as nitrogen, carbon dioxide gas and argon with air, or air solely into the gas phase portion of a storage facility (Japanese Patent Application Laid-open No. 2003-231661).

However, in fact, the above conventional methods have failed to completely prevent occurrence of troubles based on polymers of the (meth)acrylic acid or (meth)acrylic esters. According to the present inventors' knowledge, one reason therefor is that air flowing into the storage tank upon discharging the (meth)acrylic acid or (meth)acrylic esters therefrom contains suspended particulate matters (SPM). The suspended particulate matters induce polymerization of the (meth)acrylic acid or (meth)acrylic esters, resulting in production of insoluble polymers thereof.

DISCLOSURE OF THE INVENTION

Problem to be Solved by the Invention

The present invention has been made for solving the above conventional problems. An object of the present invention is to provide a method for storing (meth)acrylic acid or (meth)acrylic esters in a storage tank for receiving or discharging the (meth)acrylic acid or (meth)acrylic esters, which is capable of storing the (meth)acrylic acid or (meth)acrylic esters for a long period of time.

Means for Solving the Problem

The present invention has been attained on the basis of the above finding. To accomplish the aim, in an aspect of the present invention, there is provided a method for storing (meth)acrylic acid or (meth)acrylic esters in a storage tank for receiving or discharging the (meth)acrylic acid or (meth)acrylic esters, wherein a concentration of suspended particulate matters contained in a gas phase portion of the storage tank is controlled to not more than 0.01 mg/m$^3$.

EFFECT OF THE INVENTION

According to the method of the present invention, when the (meth)acrylic acid or (meth)acrylic esters is stored in a storage tank for receiving or discharging the (meth)acrylic acid or (meth)acrylic esters, production of insoluble polymers thereof can be effectively prevented, and as a result, the (meth)acrylic acid or (meth)acrylic esters as easily-polymerizable compounds can be stably stored in the storage tank without deterioration in quality thereof for a long period of time.

PREFERRED EMBODIMENT FOR CARRYING OUT THE INVENTION

The present invention is described in detail below. First, the (meth)acrylic acid or (meth)acrylic esters to be stored are explained.

The (meth)acrylic acid includes acrylic acid and methacrylic acid. Of these compounds, preferred is acrylic acid. In addition, the (meth)acrylic esters are not particularly restricted. Examples of the (meth)acrylic esters may include methyl(meth)acrylate, ethyl(meth)acrylate, propyl(meth)acrylate, butyl(meth)acrylate, cyclohexyl(meth)acrylate, 2-ethylhexyl(meth)acrylate, nonyl(meth)acrylate, hydroxyethyl(meth)acrylate, methoxyethyl(meth)acrylate, ethoxyethyl(meth)acrylate and dimethoxyaminoethyl(meth)acrylate. Of these (meth)acrylic esters, preferred are butyl acrylate and 2-ethylhexyl acrylate.

The method of producing the (meth)acrylic acid is not particularly restricted, and the (meth)acrylic acid may be produced by a method of subjecting a raw material such as propylene, isobutylene or t-butyl alcohol to gas-phase catalytic oxidation reaction. Also, the method of producing the (meth)acrylic esters is not particularly restricted. For example, the (meth)acrylic esters may be produced by an esterification reaction method in which (meth)acrylic acid is reacted with alcohol in the presence of a catalyst such as organic acids and cation exchange resins.

The storing method of the present invention is characterized in that when (meth)acrylic acid or (meth)acrylic esters are stored in the storage tank for receiving or discharging the (meth)acrylic acid or (meth)acrylic esters, the concentration of suspended particulate matters contained in a gas phase portion of the storage tank is controlled to not more than 0.01 mg/m$^3$.

The suspended particulate matters (SPM) contained in the gas phase portion of the storage tank mean particles having a particle size of not more than 10 μm, which are suspended or floated in air. Although the time-average concentration of the suspended particulate matters in air is usually in the range of 0.03 to 0.04 mg/m$^3$, the time-average concentration thereof tends to exceed 0.1 mg/m$^3$ depending upon locational conditions of the storage tank and time zones.

The suspended particulate matters tend to flow into the storage tank together with air sucked therein upon discharging the (meth)acrylic acid or (meth)acrylic esters from the storage tank. That is, when the (meth)acrylic acid or (meth)acrylic esters are discharged from the storage tank in the receiving or discharging step of the (meth)acrylic acid or (meth)acrylic esters, an inside of the storage tank is under a negative pressure, so that air is sucked into the storage tank through a gas suction means such as a breather valve fitted to an upper portion of the storage tank, and the suspended particulate matters entrained in the air are also flowed into the storage tank.

Upon storage of the (meth)acrylic acid or (meth)acrylic esters, for example, upon storage of ten hundred thousand tons of the (meth)acrylic acid or (meth)acrylic esters per year, the amount of the suspended particulate matters flowing into the storage tank is approximated as follows.

In the case where the (meth)acrylic acid or (meth)acrylic esters are supplied to the storage tank at a rate of 12.6 m$^3$/hr and discharged therefrom at a rate of 34.2 m$^3$/hr for 8 hr, air is sucked into the storage tank in an amount of 21.6 m$^3$/hr. The total amount of air sucked into the storage tank per year reaches 67,000 m$^3$. Assuming that the concentration of the suspended particulate matters contained in air to be sucked is 0.1 mg/m$^3$ per hour, the amount of the suspended particulate matters flowing into the storage tank reaches 6.7 g per year.

Meanwhile, the suspended particulate matters flowed into the storage tank may induce polymerization of the (meth)acrylic acid or (meth)acrylic esters, so that insoluble polymers thereof are produced and accumulated in the storage tank. The accumulated insoluble polymers tend to further promote polymerization of the (meth)acrylic acid or (meth)acrylic esters. The reason therefor is considered as follows, though it is not clearly determined. That is, a polymerization inhibitor added is consumed by polymerizable monomers which are present inside the insoluble polymers or on the surface thereof, so that the polymerization of the (meth)acrylic acid or (meth)acrylic esters is caused. Therefore, in the case where the amount of the insoluble polymers produced in the storage tank is increased, the polymerization reaction of the (meth)acrylic acid or (meth)acrylic esters is accelerated, and finally the amount of heat generated by the polymerization reaction exceeds a heat removal capacity of the system, resulting in possibility of occurrence of run away reaction which tends to cause explosion accidents.

Accordingly, it is important to reduce the concentration per an hour of the suspended particulate matters present in the gas phase portion of the storage tank, which is one factor of causing production of the insoluble polymers. Namely, the concentration per an hour of the suspended particulate matters contained in the gas phase portion of the storage tank is usually not more than 0.01 mg/m$^3$, preferably not more than 0.005 mg/m$^3$. When the concentration per an hour of the suspended particulate matters contained in the gas phase portion of the storage tank is more than 0.01 mg/m$^3$, the effect of preventing the production of the insoluble polymers in the storage tank tends to become insufficient. In addition, the concentration of the suspended particulate matters in air after dust collection is preferably as low as possible. However, when the concentration of the suspended particulate matters in air becomes too low, the differential pressure between atmospheric air and an inside of the storage tank tends to be excessively increased. Therefore, it is not required to reduce the concentration of the suspended particulate matters in air to a more than necessary extent by increasing a collecting rate of the suspended particulate matters.

The amount of the suspended particulate matters flowing into the storage tank may be reduced by the method of treating air flowing thereinto using a dust collector, for example, by treating the air passing through a gas suction means using the duct collector. More specifically, in the case where air purified by the dust collector so as to reduce the concentration of the suspended particulate matters contained therein to not more than 0.01 mg/m$^3$, is fed to the storage tank, the amount of the suspended particulate matters which are present in the gas phase portion of the storage tank, can be suitably reduced. The dust collector usable in the present invention is not particularly restricted as long as the apparatus is capable of removing the suspended particulate matters from air. Examples of the dust collecting method may include filtration dust collection, washing duct collection, centrifugal dust collection and electric dust collection. Since the amount of dusts to be collected upon purification of air is extremely small, among these methods, the filtration dust collection using a cartridge-type filter filled with glass fibers, etc., is preferred because of low installation costs and facilitated operation procedure thereof.

Meanwhile, ultrafine particles having a particle size of about 0.01 µm or less are directly discharged out of the system substantially without precipitation in the gas phase portion of the storage tank. Therefore, such ultrafine particles are preferably allowed to pass through the dust collector so as to prevent increase in differential pressure at filters, etc.

EXAMPLES

The present invention is described in more detail by Examples, but the Examples are only illustrative and not intended to limit the scope of the present invention.

Example 1

A cartridge-type filter filled with glass fiber-reinforced polypropylene fibers was fitted to a feed conduit for feeding air into a breather valve mounted onto a top of a storage tank (capacity: 1,000 kL) for storing butyl acrylate to which a receiving conduit, a discharging conduit and an external circulation conduit were directly connected. Meanwhile, as a result of the previous experiments, it was confirmed that the cartridge-type filter used had a dust collecting percentage of 95%. This indicated that the concentration of suspended particulate matters contained in air fed into the storage tank was not more than 0.0075 mg/m$^3$ (meanwhile, as a result of the past experiments, it was confirmed that the maximum time-average concentration of the suspended particulate matters in a location zone where the storage tank was installed was 0.15 mg/m$^3$). The temperature of liquid in the storage tank was controlled to 20° C. by a coil-type heat exchanger provided within the storage tank and a heat exchanger provided in the external circulation conduit.

After the elapse of one year from initiation of the storage, a strainer for an external circulation pump was opened to inspect an inside thereof and sample a solid composed of polybutyl acrylate and inorganic substances. The dried weight of the solid was about 50 g. It was suggested that most of the solid was composed of insoluble polymers produced in the storage tank prior to mounting the cartridge-type filter therein as well as suspended particulate matters mixed in the polymers. Further, after the storage condition was continued for one year, the strainer was opened again to inspect an inside thereof and sample a solid. As a result, it was confirmed that the dried weight of the solid was as small as 1 g.

Comparative Example 1

Butyl acrylate was stored using the same storage tank and associated equipments, and storing conditions as defined in Example 1 except that no cartridge-type filter was installed. After the elapse of one year from initiation of the storage, the strainer for the circulation pump was opened to inspect an inside thereof and sample insoluble polymers mainly composed of polybutyl acrylate. The dried weight of the insoluble polymers was about 1.2 kg.

What is claimed is:

1. A method for storing (meth)acrylic acid or (meth)acrylic esters in a storage tank for receiving or discharging the (meth)acrylic acid or (meth)acrylic esters, wherein a concentration of suspended particulate matters contained in a gas phase portion of the storage tank is controlled to not more than 0.01 mg/m$^3$.

2. A method according to claim 1, wherein a gas containing the suspended particulate matters at a concentration of not more than 0.01 mg/m$^3$ is supplied to the storage tank for receiving or discharging the (meth)acrylic acid or (meth)acrylic esters.

3. A method according to claim 1 or 2, wherein the (meth)acrylic acid or (meth)acrylic esters are acrylic acid, methyl acrylate, ethyl acrylate, butyl acrylate or 2-ethylhexyl acrylate.

* * * * *